US007827992B2

(12) United States Patent
Sieber

(10) Patent No.: US 7,827,992 B2
(45) Date of Patent: Nov. 9, 2010

(54) SLIP-STOP DEVICE FOR CONTINUOUS PASSIVE MOTION MACHINES

(76) Inventor: Lori L. Sieber, 16945 S. Vanilla Orchid Dr., Vail, AZ (US) 85641

( * ) Notice: Subject to any disclaimer, the term of this patent is extended or adjusted under 35 U.S.C. 154(b) by 95 days.

(21) Appl. No.: 11/831,747

(22) Filed: Jul. 31, 2007

(65) Prior Publication Data

US 2009/0032032 A1 Feb. 5, 2009

(51) Int. Cl.

| | |
|---|---|
| ***A61B 19/00*** | (2006.01) |
| ***A61G 15/00*** | (2006.01) |
| ***A61F 5/00*** | (2006.01) |
| ***A63B 23/08*** | (2006.01) |
| ***A63B 21/05*** | (2006.01) |

(52) U.S. Cl. ......................... 128/869; 128/845; 602/36; 482/79; 482/128

(58) Field of Classification Search .................. 602/32, 602/36, 23, 26, 27, 28, 16, 24, 37; 128/846, 128/869, 845; 5/621-624; 482/79, 80, 124, 482/129-130, 133, 135, 137

See application file for complete search history.

(56) References Cited

U.S. PATENT DOCUMENTS

| | | | | |
|---|---|---|---|---|
| 4,641,637 A * | 2/1987 | Rosen | ......................... | 602/35 |
| 4,834,073 A * | 5/1989 | Bledsoe et al. | ................ | 601/34 |
| 5,759,165 A * | 6/1998 | Malewicz | .................... | 602/21 |
| 6,221,036 B1 * | 4/2001 | Lucas | .......................... | 602/23 |
| 6,994,683 B1 | 2/2006 | Starr | | |
| 2005/0273022 A1 * | 12/2005 | Diaz et al. | ..................... | 601/5 |
| 2006/0030807 A1 | 2/2006 | Starr | | |

* cited by examiner

*Primary Examiner*—Patricia M Bianco
*Assistant Examiner*—Ophelia Hawthorne
(74) *Attorney, Agent, or Firm*—Quarles & Brady LLP; Gavin J. Milczarek-Desai

(57) ABSTRACT

An article and method for preventing a continuous passive motion (CPM) device from moving out of position or alignment that include a holding member adapted to pass around a portion of the CPM device and an anchoring member coupled with the holding member for retaining the CPM device holding member in position. The anchoring member is adapted to be placed under the user of the device and held fast by the weight of the user, thereby assuring secure control of the CPM device position by the user.

11 Claims, 2 Drawing Sheets

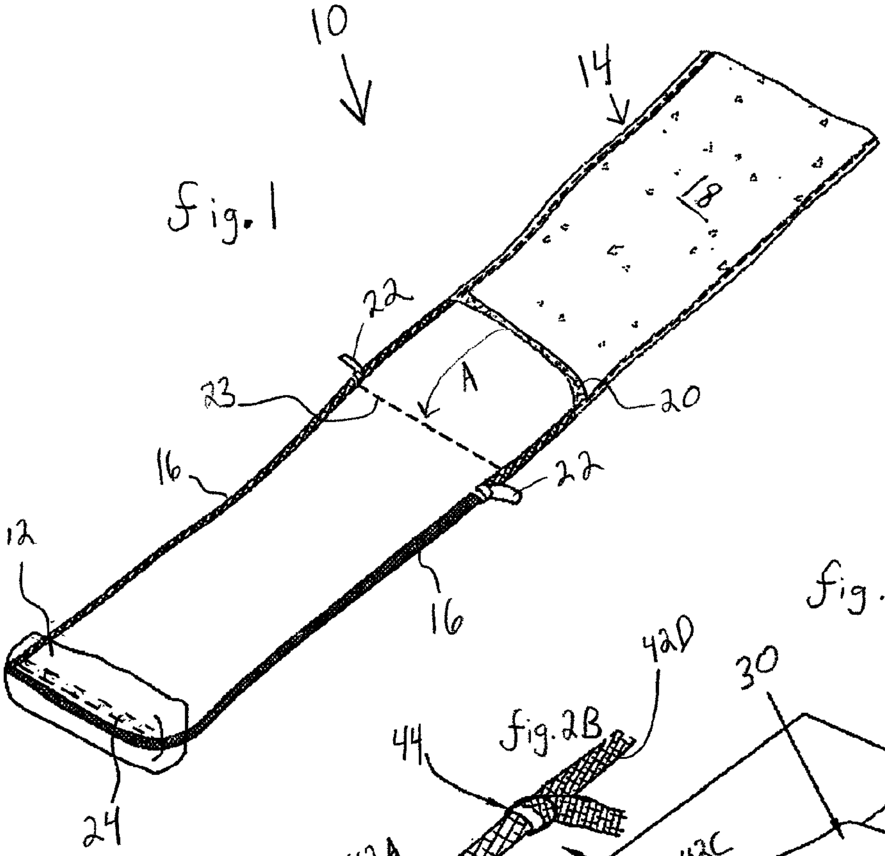
10
14
fig. 1
18
22
23
A
20
22
16
16
12
24
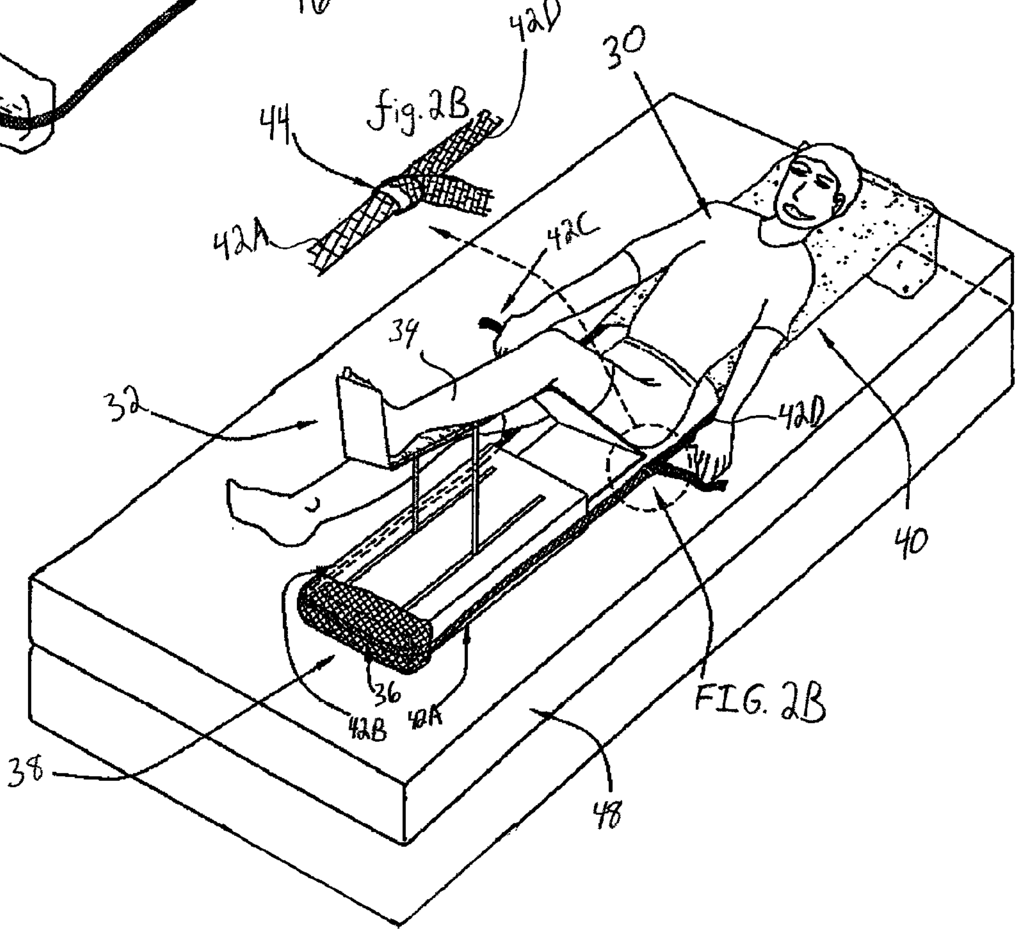
fig. 2A
fig. 2B
42D
44
42A
30
42C
34
32
42D
40
36
42B
42A
FIG. 2B
38
48

SLIP-STOP DEVICE FOR CONTINUOUS PASSIVE MOTION MACHINES

BACKGROUND OF THE INVENTION

1. Field of the Invention

The invention relates generally to a device for anchoring a Continuous Passive Motion ("CPM") device in place.

2. Description of the Related Art

Continuous Passive Motion (CPM) devices are commonly used to exercise and rehabilitate a bodily joint or extremity that has been injured and surgically or otherwise treated. For example, CPM devices are used to prevent muscular atrophy, to improve flexibility, and to help restore a full range of motion to patients who have undergone knee surgery.

A common problem in physical therapy situations is that the CPM device used to exercise healing joints often "creeps" along the treatment area or otherwise slips out of proper alignment with the joint. This leads to discomfort and possible injury.

In the past, clamps and other mechanical ways of anchoring a CPM in place have been used. However, it continues to be desirable for there to be ways of positioning a CPM device in a less complicated manner and in a fashion that allows the patient to adjust such positioning.

SUMMARY OF THE INVENTION

The invention relates in general to an article and method that involve "patient-anchoring" of a continuous passive machine. More particularly, the article includes an arrangement having a holding member adapted to pass around a portion of the CPM device to inhibit movement of the device relative to a user of the device along at least one direction and an anchoring member coupled with the holding member for retaining said CPM holding member in position. The anchoring member is adapted to be placed under a user of the device and held fast by the weight of the user. Thus, the position of the CPM device is kept substantially constant in a manner that does not require clamps or the like.

Preferably, the holding member and the anchoring member are movable relative to one another so as to permit adjustment of the relative position of the holding member and the anchoring member to a user of the CPM device (for example, to adjust for user height).

In one aspect of the invention, the holding member and the anchoring member are each provided with a connecting element, with the connecting elements being releasably connectable to one another so as to permit releasable attachment of the holding member to the anchoring member. So, for example, connecting elements may comprise straps, which may include a ring for adjusting the strap length. Thus, the position of CPM device may be adjusted by the user. In other embodiments, a hook-and-loop fastener may be used to adjust the position of the anchoring member relative to the holding member as illustrated below.

In another aspect of the method of the invention, the anchoring member may include a planar sheet that is adapted to be placed under a user of the device and held fast by the weight of the user. In such an embodiment, the anchoring member preferably includes a pair of straps attached to the holding member at opposing ends thereof. Alternatively, a second pair of straps also may be connected to the anchoring member. Thus, each pair of straps can be joined (with, for example, a ring or buckle) such that the anchoring member and holding member are adjustably coupled.

In still another aspect of the invention, a method for preventing a continuous passive motion (CPM) device from moving out of alignment with a user is provided. The method includes (1) providing a holding member adapted to pass around a portion of the CPM device and having an anchoring member coupled with the holding member for retaining the CPM device holding member in position, (2) securing the holding member to the CPM device, and (3) positioning the user on the anchoring member such that it is held fast by the weight of the user.

The methods of the invention may further include steps directed to adjustment of the distance between the holding member and the anchoring member while the CPM device is in use (to keep the position of the CPM device substantially constant relative to the position of the user) and having the adjustment step performed directly by the user. Thus, the invention provides a new and improved arrangement and method for assisting a user in holding a CPM device in proper position and alignment during physical therapy.

The arrangement and method are particularly useful in situations in which the user is supine and having a leg exercised by a CPM device, thereby minimizing any anxiety about the device "creeping" or otherwise misaligning by enabling the user to control the position of the device (particularly while the user is left alone).

Various other purposes and advantages of the invention will become clear from its description in the specification that follows. Therefore, to the accomplishment of the objectives described above, this invention includes the features hereinafter fully described in the detailed description of the preferred embodiments, and particularly pointed out in the claims. However, such description discloses only some of the various ways in which the invention may be practiced.

BRIEF DESCRIPTION OF THE DRAWINGS

FIG. 1 is perspective view of an embodiment of the invention.

FIG. 2A illustrates in perspective view the embodiment of FIG. 1 with a user of the embodiment disposed thereon.

FIG. 2B is a magnified view of the section of FIG. 2A circled in phantom line.

DETAILED DESCRIPTION OF THE PREFERRED EMBODIMENTS

Figure 3:
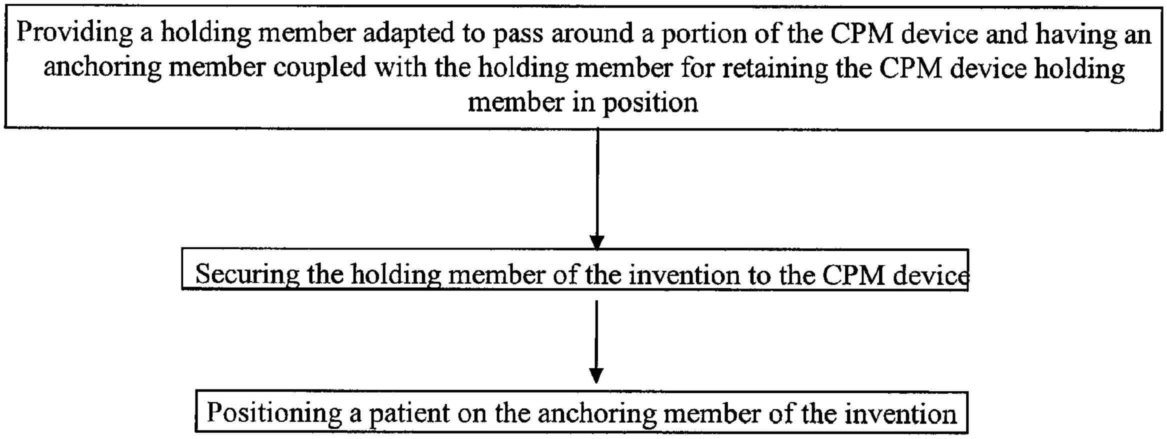
FIG. 3 illustrates in flow diagram the basic steps of a method of the invention.

Referring to FIG. 1, the numeral 10 identifies an arrangement in accordance with the invention for holding a CPM device in place.

The arrangement 10 includes a holding member 12 adapted to pass around a portion of the CPM device (see FIG. 2A) to inhibit movement of the device and an anchoring member 14 coupled with the holding 12 member by, for example, straps 16 for retaining the holding member 12 in position. The anchoring member 14 is adapted to be placed under a user (preferably the user's torso) of the CPM device and held fast by the weight of the user. Thus, the anchoring member 14 may be planar sheet 18 and disposed beneath a supine user as shown in FIG. 2A.

Preferably, the holding member 12 and the anchoring member 14 are movable relative to one another so as to permit adjustment of the relative position of the holding member and the anchoring member to a user of the CPM device. Thus, for example, hook fastener 20 may be secured to loop fastener tabs 22 (so that the anchoring member 14 is adjusted to position 23 as indicated by arrow A) or to the loop fastener strip 24 at the bottom edge of holding member 12, thereby causing the holding member 12 and anchoring member 14 to be directly joined.

Turning to FIG. 2A, a typical rehabilitation situation is depicted in which patient 30 is using CPM device 32 to exercise a leg 34 after knee surgery. The holding member 36 (which preferably includes receptacle portion 38) and the anchoring member 40 are each provided with a connecting element (in this case, straps 42A and 42B attached at opposing ends of holding member 36 and straps 42C and 42D attached to an edge of anchoring member 40), with the connecting elements 42A-42D being releasably connectable to one another so as to permit releasable attachment of the holding member 36 to the anchoring member 40.

As is best seen in the magnified view of FIG. 2B, each pair of connecting elements 42A-42D further includes a ring 44 that enables to patient 30 to adjust the length of the elements. Accordingly, the patient 30 can independently control the alignment of the CPM device to increase comfort and reduce the possibility of injury. Moreover, the tendency of the CPM device 32 to "creep" along bed 48 is effectively prevented, both by the patient's weight upon anchoring member 40 and through pulling on straps 42C and 42D.

As shown in FIG. 3, a simplified schematic of a basic method for preventing a continuous passive motion (CPM) device from moving out of alignment with a user is shown. First, a holding member adapted to pass around a portion of the CPM device and having an anchoring member coupled with the holding member for retaining the CPM device holding member in position is provided. In either order, the holding member is secured to the CPM device and the user is positioned on the anchoring member such that the user's weight holds fast the holding member (and, therefore, the CPM device) in position.

Preferably, an adjustable slip-stop arrangement is provided so that the user will be able to adjust the distance between the holding member and the anchoring member before and while the CPM device is in use to keep the position of the CPM device substantially constant relative to the position of the user.

Various changes in the details and components that have been described may be made by those skilled in the art within the principles and scope of the invention herein described in the specification and defined in the appended claims. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and products.

What is claimed is:

1. A combination of a continuous passive motion (CPM) device disposed atop a surface and an arrangement for restraining a continuous passive motion device from moving relative to the position of a user of said device, comprising:

a holding member that passes around a portion of and is thereby secured to the CPM device; and an anchoring member coupled with said holding member for retaining said CPM holding member in position, said anchoring member comprising a planar sheet that is placed under the user of the device and held fast by the weight of the user such that the position of the CPM device on said surface is held substantially constant relative to the position of the user when said user is atop the planer sheet, wherein said holding member and said anchoring member are each provided with a connecting element, said connecting elements being releasably connectible to one another so as to permit releasable attachment of said holding member to said anchoring member.

2. The combination of claim 1, wherein one of said connecting elements comprises a strap.

3. The combination of claim 2, wherein said one connecting element further comprises a ring attached to said strap.

4. The combination of claim 1, wherein said holding member and said anchoring member are movable relative to one another so as to permit adjustment of the relative position of said holding member and said anchoring member to a user of the CPM device.

5. The combination of claim 1, wherein said holding member comprises a receptacle for a portion of the CPM device.

6. A combination of a continuous passive motion (CPM) device disposed atop a surface and an arrangement for restraining a continuous passive motion device from moving relative to the position of a user of said device comprising:

a holding member including a receptacle portion that passes around a portion of and is thereby secured to the CPM device; and an anchoring member coupled with said holding member for retaining said CPM holding member in position, said anchoring member comprising a planar sheet that is placed under the user of the device and held fast by the weight of the user such that the position of the CPM device on said surface is held substantially constant relative to the position of the user when said user is atop the planer sheet.

7. The combination of claim 6, wherein said anchoring member includes a pair of straps attached to said holding member at opposing ends thereof.

8. The combination of claim 7, wherein said holding member and said pair of straps are movable relative to one another so as to permit adjustment of the relative position of said holding member and said anchoring member to a user of the CPM device.

9. The combination of claim 6, wherein said holding member and said anchoring member are each provided with a pair of connecting elements, said connecting elements being releasably connectible to one another so as to permit releasable attachment of said holding member to said anchoring member.

10. The combination of claim 9, wherein each of said pair of connecting elements includes a ring for adjusting a length of said elements.

11. The combination of claim 6, wherein said holding member and said anchoring member are movable relative to one another so as to permit adjustment of the relative position of said holding member and said anchoring member to a user of the CPM device.

* * * * *